United States Patent [19]

Robinson

[11] Patent Number: 4,604,762
[45] Date of Patent: Aug. 12, 1986

[54] ARTERIAL GRAFT PROSTHESIS

[75] Inventor: Thomas C. Robinson, Berkeley, Calif.

[73] Assignee: Thoratec Laboratories Corporation, Berkeley, Calif.

[21] Appl. No.: 234,116

[22] Filed: Feb. 13, 1981

[51] Int. Cl.[4] ............................ A61F 1/00; A61F 1/24
[52] U.S. Cl. ..................................... 623/1; 128/334 R
[58] Field of Search ................... 3/1.4, 1, 1.5; 128/334 R

[56] References Cited

U.S. PATENT DOCUMENTS

| | | | |
|---|---|---|---|
| 3,460,975 | 8/1969 | Stebleton | 3/1.4 X |
| 3,511,684 | 5/1970 | Huffaker | 3/1.4 X |
| 3,730,835 | 5/1973 | Leeper et al. | 3/1 X |
| 4,101,984 | 7/1978 | MacGregor | 3/1 X |
| 4,130,904 | 12/1978 | Whalen | 3/1.4 |
| 4,173,689 | 11/1979 | Lyman et al. | 3/1.4 X |
| 4,281,669 | 8/1981 | MacGregor | 128/784 |
| 4,306,318 | 12/1981 | Mano et al. | 3/1.4 |
| 4,355,426 | 10/1982 | MacGregor | 3/1.4 |

FOREIGN PATENT DOCUMENTS

| | | | |
|---|---|---|---|
| 1068052 | 12/1979 | Canada | 3/1.5 |
| 1092303 | 12/1980 | Canada | 3/1.4 |
| 2913510 | 10/1979 | Fed. Rep. of Germany | 3/1.4 |
| 135493 | 10/1979 | Japan | 3/1.4 |
| 0088760 | 7/1980 | Japan | 3/1.4 |

Primary Examiner—Ronald L. Frinks
Attorney, Agent, or Firm—Flehr, Hohbach, Test, Albritton & Herbert

[57] ABSTRACT

An arterial graft prosthesis comprises a first interior zone of a solid, segmented polyether-polyurethane material surrounded by a second zone of a porous, segmented, polyether-polyurethane and a third zone immediately surrounding said second zone and of a solid, segmented polyether-polyurethane. The interior zone may have a lining or blood interface of a microporous zone of segmented polyether-polyurethane, and the exterior, third zone may be surrounded by a tissue interface of a microporous zone of segmented polyether-polyurethane. In some instances the exterior may be confined by a tube of substantially non-stretchable netting fastened in place at chosen, spaced intervals or other forms of reinforcement may be employed. Other materials can be used.

5 Claims, 17 Drawing Figures

ARTERIAL GRAFT PROSTHESIS

BACKGROUND OF THE INVENTION

Prosthetic arterial grafts have been available to the medical profession for thirty years or more. However, during that thirty years the development of such grafts have been limited to those formed of textile fabrics and of semi-rigid plastics such as Teflon which have been made somewhat flexible by distension or stretching so that microscopic pores are produced which, although too small to permit the passage of blood, do permit some degree of flexibility. Such porosity does allow such grafts to eventually leak under certain conditions. Textile arterial grafts are generally a single tubular structure. Arterial graft prostheses of stretched, semi-rigid plastics have been made of multiple parts or tubes but the resultant structure has not been homogeneous or attached so that it may be separable under normal conditions of use such as during the suturing of the graft in place.

In the development of an arterial graft prosthesis it must be recognized that the optimal prosthesis should have static and dynamic elastic moduli and pressure distension in both the radial and axial directions which closely match those for normal human arteries of the same diameter. Moreover, the wall thickness should be very close to that of the human artery and should resist kinking when bent as well as do natural arteries. The prosthesis should have uniform homogeneous physical properties fully along its length so that the surgeon may cut any length he desires. Moreover, it should be easily sutured with the same needle penetration force and suture pull through force as is required with natural arteries. The suture should not pull out nor tear to any greater extent nor with any less force than with the natural artery. The prosthesis should be impervious to blood not only along the major portion of its length but also where the customary needle holes are placed during suturing. This, particularly, has not been possible with graft prosthesis of the prior art in which leaking at suture points usually exists until a thrombus is formed. Moreover, the prosthesis should inhibit tissue growth throughout the graft structure which would result in the stiffening of the graft itself. It should be compatible with blood and tissue and should also provide attachment to external tissues for fixation and avoidance of trapped fluids inside a loose tissue capsule. The graft should remain patent and unobstructed indefinitely without any inherent clot or generation of thromboemboli. These objectives have not been met by the arterial graft prosthesis of the prior art.

BRIEF SUMMARY OF THE INVENTION

A representative arterial graft prosthesis in accordance with the invention comprises at least two concentric zones of elastomer material homogeneously joined together to form a single tube with the elastomer in one of the zones being porous. In other embodiments such a tube is, in turn, surrounded by a third zone of a solid, segmented elastomer. Also, the interior surface or the exterior surface, or both, of the mentioned three-zone tube may also be augmented from time to time and for different conditions.

DETAILED DESCRIPTION

Figure 1:
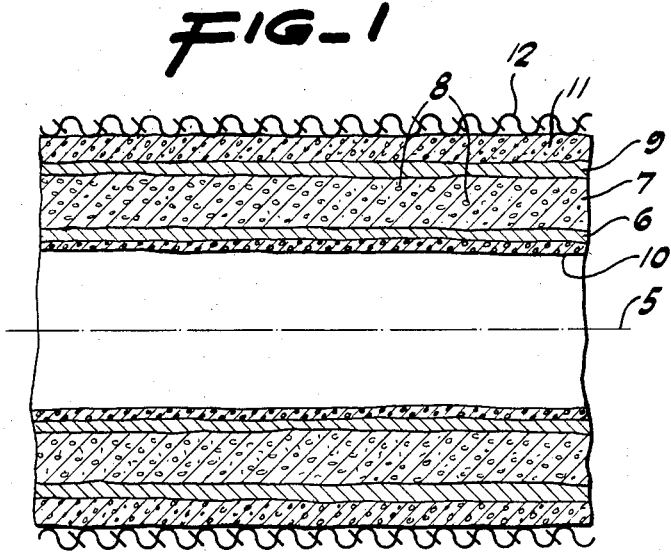
FIG. 1 is a longitudinal, diametrical cross section of a composite arterial graft showing not only the three mentioned zones of segmented elastomer but also an interior and exterior lining zone and an exterior confining reinforcement.

While the drawings herein show the various zones of the arterial graft separated by solid lines, it must be recognized that the zones are homogeneously attached to each other while the substance of at least one of the zones is in a liquid or semi-liquid state. The various zones are formed of the same general material such as polyurethane. The polyurethane is dissolved in a solvent and applied as a viscous liquid. The solvent within the liquid penetrates the surfaces of the attached zones and provides for homogeneous mixing of the polymers and adhesion as if it were of one material. Consequently, the interface between zones has some finite dimension of thickness not shown in the drawing and having a composition which is a blend of the two adjacent zones.

In the representative version of the arterial graft shown in FIG. 1, there is provided, symmetrical with a center line 5, an inside tubular zone 6. This is a generally impervious zone of a segmented polyether-polyurethane material which is continuous and is largely a barrier to the various liquid materials with which it is normally associated. The zone 6 is approximately one to six mils in radial thickness and is generally a radial bar to the blood which flows through the graft under normal pressures and actions.

Directly surrounding the tubular zone 6 there is an intermediate zone 7 also fundamentally of polyether-polyurethane but preferably of somewhat greater thickness—generally from 10 to 80 mils. The zone 7 is of a porous nature, being from thirty percent to ninety percent void or open volume. The void volume may be of uniformly sized and distributed pores with the pores 8 ranging from one to one hundred fifty microns in size.

Usually, the intermediate zone 7 is directly surrounded by an encompassing or outward zone 9. This also is of a segmented polyether-polyurethane material corresponding to that in the zone 6 and having a lack of pores or orifices, being continuous like the zone 6 and so distinguished from the porous zone 7. The radial dimension of the zone 9 is from one to six mils. The portions of this form of substitute blood vessel thus far described are all made of segmented polyether-polyurethane zones of different sizes and with the central zone, only, containing a number of cells or spaces or voids.

Reference herein is made primarily to the zones being of a segmented polyether-polyurethane material, and that has proved to be most satisfactory in practice. It must be noted, however, that of the numerous elastomers available (for example, silicone rubber) in various instances there may be used elastomers that are not segmented and are not polyesters nor polyethers. Much of the actual work herein has been done with a segmented polyether-polyurethane material, specifically such material sold under the trademark "Biomer", and so, for convenience, those materials are referred to herein. Yet, it must be recognized that comparable and substitute materials may be used or may become available.

Construction of an arterial graft prosthesis, as defined herein, results in static and dynamic moduli and pressure distortions in both radial and axial directions closely to match such distensions of normal human arteries of comparable diameter. Consequently, even after clamping, the prosthesis of the present invention, unlike the prior art prostheses, recover in the same manner as do natural arteries. Also, the wall thickness used is very close to that of human arteries of a comparable diameter. Furthermore, these prostheses, when formed, resist kinking when bent as well as the normal, natural arteries. There are uniform, homogeneous physical properties along the entire length of the insert or graft, so that the surgeon can cut an insert to any length he desires with uniform results.

The prostheses defined suture as easily and with substantially the same needle penetration force and suture pull-through force as in the case of natural arteries. Also, sutures made in the prostheses do not pull out or tear to any greater extent or with any less force than those in a natural artery. The grafts defined, when formed, are impervious or leak tight to the circulating blood. The customary needle holes are substantially immediately self-closing, so that they do not leak any contained blood. Furthermore, the prostheses inhibit tissue growth throughout the graft structure and so prevent a resultant stffening of the graft. They readily provide appropriate fixation for external tissue attachment and ready avoidance of trapped fluids inside the tissue capsule. The prostheses are quite compatible with the customary blood and adjacent tissues. Also, the formed, indicated prostheses generally remain open and unobstructed indefinitely and without any adherent clot or the generation of internal thromboemboli. The net result is that the described prostheses afford an arterial replacement which is in most respects virtually indistinguishable from the original native artery.

In addition to the zones 6, 7, and 9, the embodiment of FIG. 1 also includes a microporous blood interface 10. In an arterial graft of approximately six millimeter internal diameter or more, the blood interface 10 may comprise a zone of "Biomer", having interior pores of a diameter and depth ranging from five to one hundred microns, approximately. Preferably, the microporous tissue is treated to be hydrophilic or hydrophobic, for instance, by subjection to known gas plasma or electrical discharge methods. The so-treated microporous tissue interface is effective as an anchoring substrate for a developing pseudointima which forms blood constituents. This pseudointima is a tissue layer which must adhere to the blood interface and remains quite thin. If desired, the hydrophilic or hydrophobic microporous blood interface may be coated with an antithrombin such as albumin, gelatin, glycoproteins, bonded heparin or comparable material to prevent or to diminish any early thrombus formation. Such initial coatings, in use, may gradually be replaced with the developing pseudointima as described.

About the outside of the graft is an adherant surrounding tissue interface 11. The material of the interface 11, like the blood interface 10, may also be a microporous "Biomer" but with slightly larger pores—in the range of thirty to one hundred fifty microns. The surface of this interface may also and similarly be made hydrophilic or hydrophobic.

Particularly for the porous core 7 but also for the interfaces 10 and 11, the homogeneous pores are initially formed by the use of particulates such as salt (NaCl) or sodium bicarbonate, which is ultimately largely removed by diffusion in a water or very dilute acid bath. The sodium bicarbonate also acts as a blowing agent in that the $CO_2$ is released and thus decreases the amount of salt to be removed from the core. The particulates utilized for this purpose are screened to afford a very narrow range of sizes, so that the pore sizes themselves are confined to a very narrow range. The result is a porous or foam-like structure containing closed-cell or open-cell voids with a substantially reduced general density.

The salt particles, for example, and the "Biomer" or core solution are completely and homogeneously mixed to form a slurry. Different slurries, with or without salt particles, are then used to form the various zones on a mandrel. The first slurry (with salt or sodium bicarbonate particle size to produce pores of from five to one hundred microns) is applied directly to the mandrel by dipping, coating or doctoring to form the zone 10. This is followed by an unsalted solution to form the zone 6 and the sequence is continual until the entire graft is fabricated. The coatings on the mandrel are then thoroughly dried to remove the solvent and then the salt or bicarbonate particles are removed in a water bath at about 60° C. There are water-filled voids so created by the dissolution and diffusion of the salt particles. The particle size and concentration of particles are arranged to control the density or porosity and pore size. For example, sodium chloride particles of about fifty micron average size are used for the zone 7 and the optimum range is within about one to one hundred fifty microns. The total void volume is about fifty percent of the total layer volume, the range being from about thirty percent to ninety percent.

The result of the foregoing is the production of a readily patent and clinically superior tubular graft which simulates very closely the properties of a natural artery. This provides that the artificial graft can be sutured to adjacent arteries very much as though a natural artery were utilized. The dimensional and distensional simulation by the artificial material to the natural material reduces or eliminates sutureline discontinuities and obstructions. Furthermore, grafts of the present prostheses behave very much like the natural artery, so that the surgeon's skill and experience are fully utilized. Also, the grafts of the present prostheses provide the same suturability, freedom from kinking, clamping characteristics, impermeability, biocompatability, antithrombogenicity, patency, and other advantages of natural arterial material.

Although the present artificial construction has two or often three zones, nevertheless the several zones allow for the provision of individual or separate component characteristics, preferably all based on the polyether-polyurethane structure.

In some instances, it is desirable to surround the exterior of the artificial artery so provided with a confining netting 12 of "Dacron" or the like or a circumferential winding of a suitable filament 13 (see FIG. 2) which may be formed of "Dacron", solid elastomer, wire or the like. When external, as in FIG. 1, this reinforcement is customarily adhesively affixed at spaced intervals and loosely surrouds the remainder of the artificial artery. The netting comes into play primarily only in the event there is a substantial expansion of the artery. The netting confines the amount of such expansion to preclude undue stretching and thinning of the artery walls.

Figure 2:
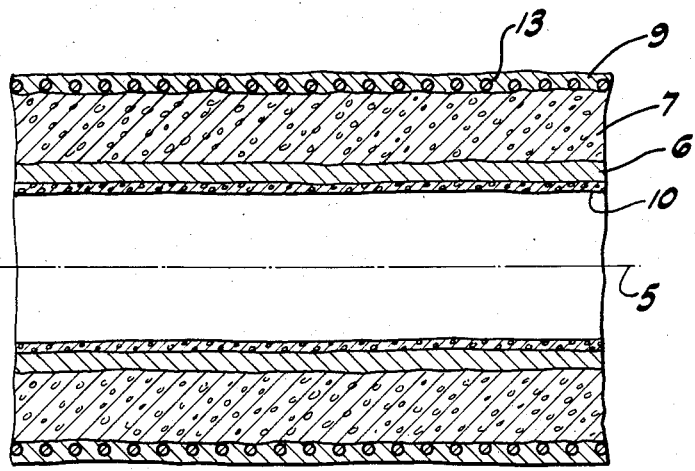
FIG. 2 is a view comparable to FIG. 1 but in which the confining reinforcement, instead of being external and of woven material, is internal and of a helically wrapped thread.

As an alternative to the attachment of the reinforcing material to the outer zone of the prosthesis, as shown in FIG. 1, it may be formed within one or more of the zones of elastomer as particularly shown in FIG. 2, the purpose here also being to preclude undue expansion of the artificial artery.

Clinical experience has indicated that an artificial artery constructed as described herein and particularly fabricated primarily of polyether-polyurethane is virtually indistinguishable from the naturally occurring artery which it replaces and affords a long-term, effective and trouble free substitute for the originally occurring, natural artery.

The alternative embodiment of FIG. 2 differs from that of FIG. 1 not only in the type of reinforcing material, but also in that the tissue interface 11 is eliminated.

Figure 3:
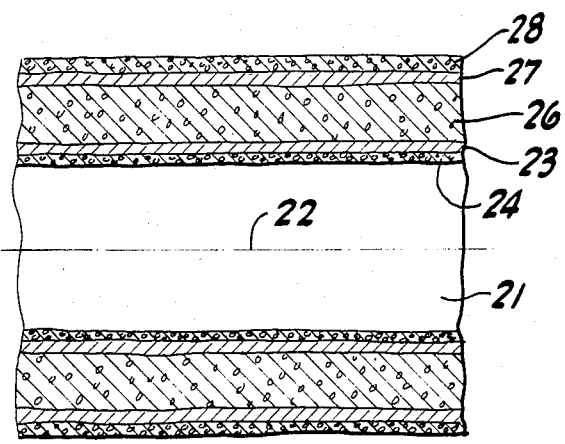
FIG. 3 is a view comparable to FIG. 1 but without reinforcement.

Another modified graft as shown in FIG. 3 is a section 21 acting as an artery generally symmetrical about a longitudinal axis 22 and particularly inclusive of an inside zone 23 of relatively solid polyether-polyurethane, preferably of segmented polyether-polyurethane. The zone 23 is arranged symmetrically about the axis 22 or approximately so and on its inner surface is covered particularly with an inner coat 24 of a micro porous blood interface of polyether-polyurethane. The pores in the interface coat 24 are in the range of five to one hundred microns in size and depth, and the coat itself is treated primarily to be hydrophilic.

The inside zone 23 and the inside coat 24 line a tubular zone or body 26 of a porous, segmented polyether-polyurethane having pores of about one to one hundred fifty microns in size. The pores are sufficient in number and disposition to allow from about thirty percent to ninety percent of the zone 26 to consist of pores.

Around the tubular body 26 there is a further zone 27 of relatively solid polyether-polyurethane about one to six mils thick. Finally, surrounding the zone 27 there is a generally exposed microporous tissue interface 28 comprised of polyether-polyurethane having pores of about thirty to one hundred fifty microns in size and depth. This exterior interface 28 likewise is treated to be hydrophilic.

It is found that with these materials and this general arrangement and construction, many of the objects of the invention are attained in an acceptable fashion. The size characteristics of the structure are well fixed and remain stable over a very long time. The wall thickness is close to that of natural human arteries of similar duties and diameters, and the materials resist kinking when bent around short-radius curves at least as well as natural arteries do. The material is uniform throughout its length, so that a fabricated tube can be cut for use of any selected portion. The material sutures easily and with similar needle techniques to those used with natural arteries. The material does not rip nor tear any more easily than natural arteries do. Further, the materials utilized provide a wall which is virtually impervious or leak-tight to blood. Tissue does not tend to grow into or stiffen the material after installation.

It is therefore quite possible by utilizing the lay-up shown in FIG. 3 and utilizing the materials specified in connection therewith and of the nature, size and characteristics stated to provide an excellent, long-term, readily handled and effective substitute for natural arteries.

Figure 4:
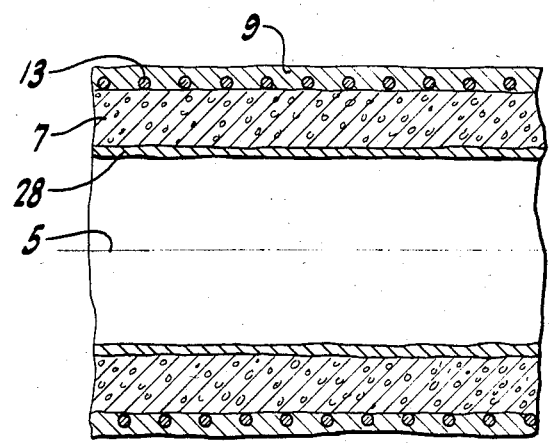
FIG. 4 is another view comparable to FIG. 2 but with some small variations.

The arrangement of FIG. 4 is very similar to that of FIG. 2. It differs in that the microporous blood interface is eliminated. In the embodiment of FIG. 4, the impervious inner zone 28 may be formed of polyether-polyurethane having an ultrasmooth surface treated by gas plasma methods, for instance, to obtain an optimal hydrophobic surface. With such a construction, the embodiment of FIG. 4 is particularly suited to grafts of 5 mm internal diameter and smaller. Such smaller grafts may not be able to sustain a pseudointima without substantial risk of occlusion and the smooth hydrophobic surface will serve to prevent thrombus formation. Such antithrombogenic surfaces may remain "clean" except for a thin glycoprotein layer.

Figure 5:
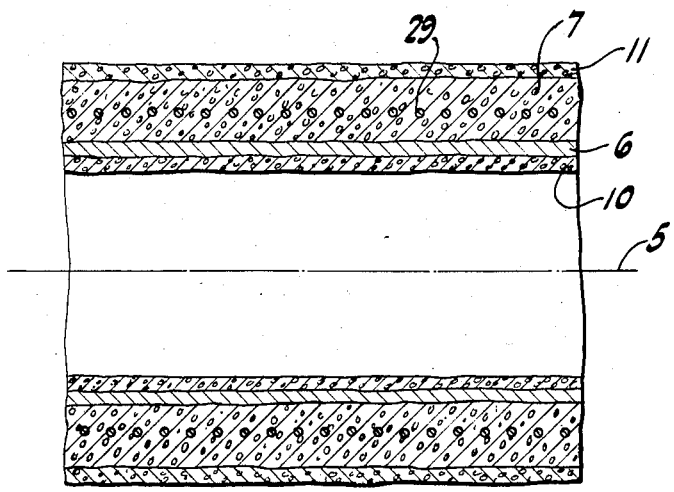
FIG. 5 is a longitudinal, diametrical cross-section showing a preferred variation having reinforcement in the porous zone.

The embodiment of FIG. 5, a preferred embodiment, is very similar to that of FIG. 1. The latter embodiment differs from the former in that a spiral reinforcement 29 is disposed in the intermediate porous zone 7 rather than a net reinforcement about the outer porous zone 11. Moreover, in the embodiment of FIG. 5, the impervious zone 9 is eliminated. While the embodiment of FIG. 5 includes a microporous blood interface 10, it should be understood that a hydrophobic copolymer could be added, particularly on small grafts. The spiral reinforcement 29 improves the anti-kinking characteristics of the graft; achieves an adequate radial elastic modulus and at the same time avoids any sharp or spiny protrusions when the graft is cut through. To this end it has been found that the tensile elastic modulus of the spiral reinforcement filament itself should be in the range of from 10,000 to 2,000,000 psi. Moreover, the ratio of the distance between spiral loops (the pitch of the spiral) to the diameter of the filament itself should be in the range of from 1.5 to 5.

Figure 6:
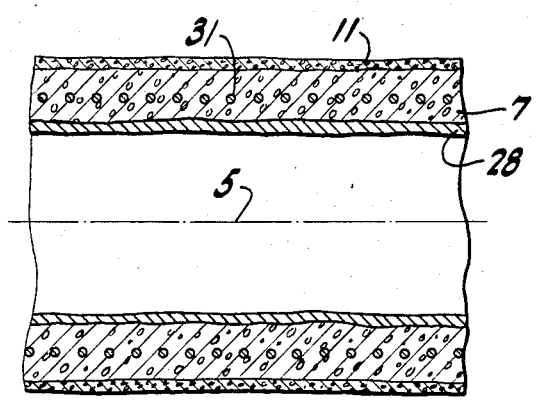
FIG. 6 shows a preferred embodiment particularly adapted to small diameter grafts.

The embodiment of FIG. 6 is particularly suited for small grafts. In this instance the structure closely resembles that of FIG. 5 but the blood interface 10 is eliminated. With such a structure the inner impervious zone 28, comparable to the zone 6 in FIG. 5, may be treated to make its surface hydrophobic and thus blood compatible. Grafts constructed in accordance with this embodiment may have an internal diameter as small as one millimeter.

Figure 7:
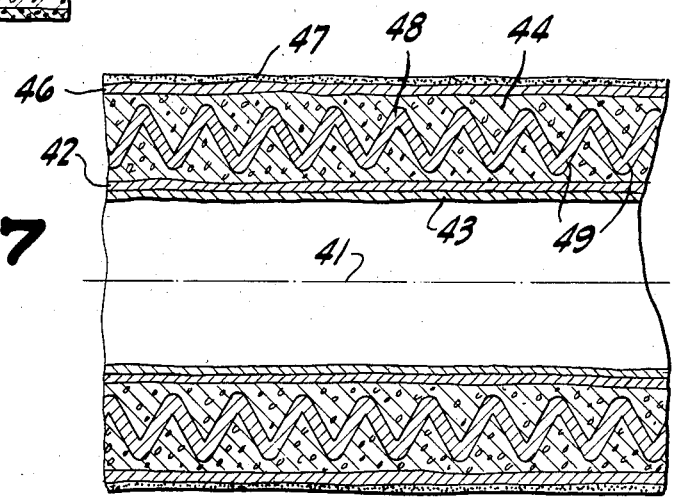
FIG. 7 is a view comparable to FIG. 1 but having a corrugated internal construction.

There may be another alternate structure of the tubular substitute artery provided, as shown in FIG. 7. In this instance the interior is symmetrical about an axis or center line 41 as before. The axis is generally symmetrically surrounded by a circular, thin solid elastomer zone 42 of segmented polyether-polyurethane. In this instance the zone 42 may be clear or lined—if lined, then having another solid elastomer zone 43 on the interior thereof. Surrounding the zone 42 there is a relatively thick, generally porous, annular zone 44. This, in turn, is surrounded by an external zone 46 of a thin solid elastomeric material in turn encased in a porous elastomer zone 47. A unique feature in this instance is that the major generally porous zone 44 is especially augmented by an enclosed, longitudinally extending, solid or high density porous elastomer 48 formed with corrugations 49, the corrugations being either parallel and circular or contoured in a spiral path.

Figure 8:
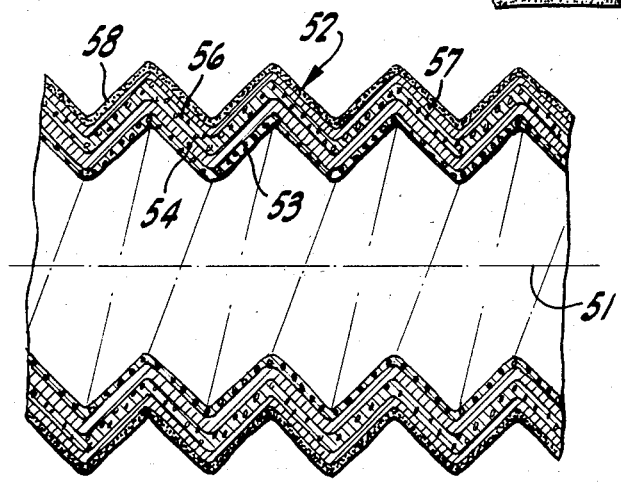
FIG. 8 is a view like FIG. 7 but in which the entire construction is corrugated.

While it is usually customary to provide each of the vessels as a symmetrical construction of relatively unlimited length and extending along a central axis 51, the configuration need not include an entirely cylindrical enclosure as shown in FIG. 8. For example, and especially for use in relatively large diameter grafts; i.e. over eight millimeters inside diameter, there can be provided a zone setup very much as previously described but with the zones configured around the axis 51 in a convoluted structure 52. That is, the interior surface need not be generally smooth, but may be undulatory or corrugated, with the different undulations either having parallel circumferential paths or joined in a spiral path. In this instance, as before, the inner blood contacting surface 53 may be a microporous blood interface. Next adjacent is a solid elastomer zone 54, while surrounding that is a porous elastomer zone 56 of medium density. Around that next to the outside there is an impervious zone 57, and finally a porous elastomer tissue interface or zone 58 on top of everything. The embodiment of FIG. 8, then, is similar to that of FIG. 1 except that the reinforcement 12 of FIG. 1 is replaced by the corrugated configuration of the overall prosthesis. It should be recognized that the reinforcement of other embodiments described above, such for example, as that of FIG. 5, may also be replaced by the corrugated configuration as shown in FIG. 8. Such configuration are particularly suitable for grafts having an internal diameter of from about 10 to 30 millimeters.

Figure 9:
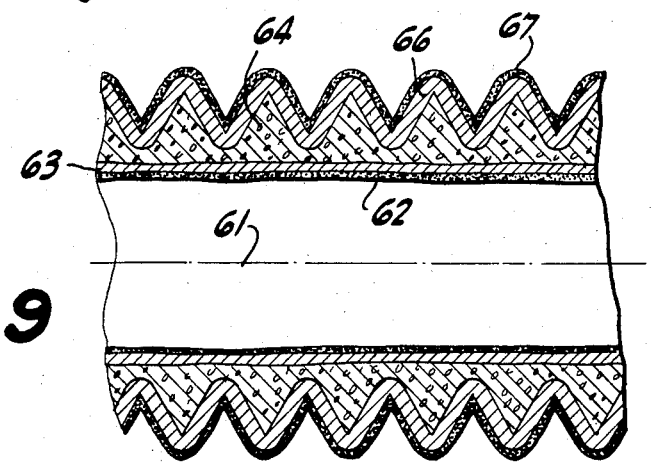
FIG. 9 is a view like FIG. 7 but in which the exterior is crrugated, while the interior is smooth.

In another variation, as particularly shown in FIG. 9, there is a vessel symmetrical about a central axis 61. The inside zone 62 is formed of a porous elastomer. Encasing this is a solid elastomer zone 63 which, in turn, is surrounded by a porous elastomer zone 64. The zone 64 is encased by a solid elastomer, undulatory zone 66 itself coated or surrounded by an external zone 67 of a microporous tissue interface. Alternatively, the inner zone 62 may be eliminated and the smooth surfaced impervious zone 63 treated to be blood compatible.

Figure 11:
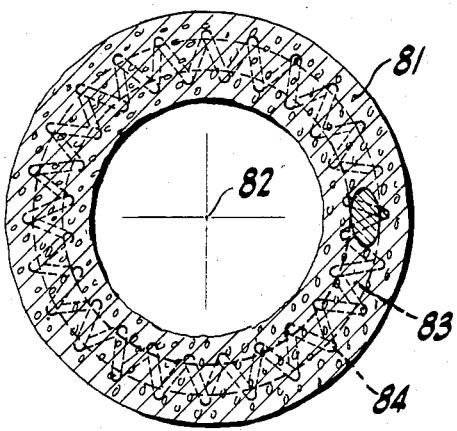
FIG. 11 is an end view of the structure of FIG. 10 with a portion broken away to show the interior construction.
Figure 10:
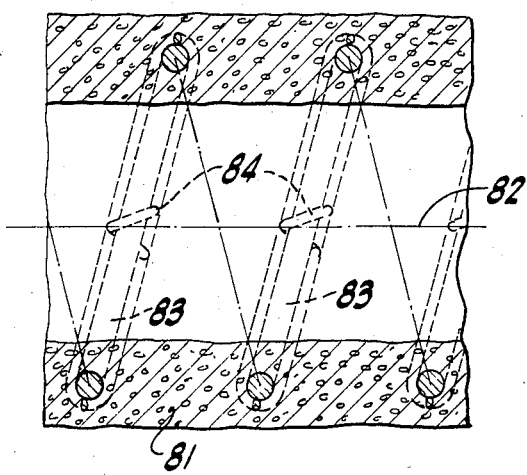
FIG. 10 is another variation showing reinforcement in the form of hoops which are helical and augmented.

A somewhat different approach is shown in FIGS. 10 and 11. An encasing wall shown generally at 81 is of a suitable material and multiple zones as previously described. Embedded in the wall and symmetrical about the central axis 82 is a helical reinforcement 83. This is preferably fabricated of a solid or quite dense porous elastomeric material. The reinforcement 83 in turn can also be wrapped with a helical filament 84 comprised of plastic thread or metal wire.

Figure 12:
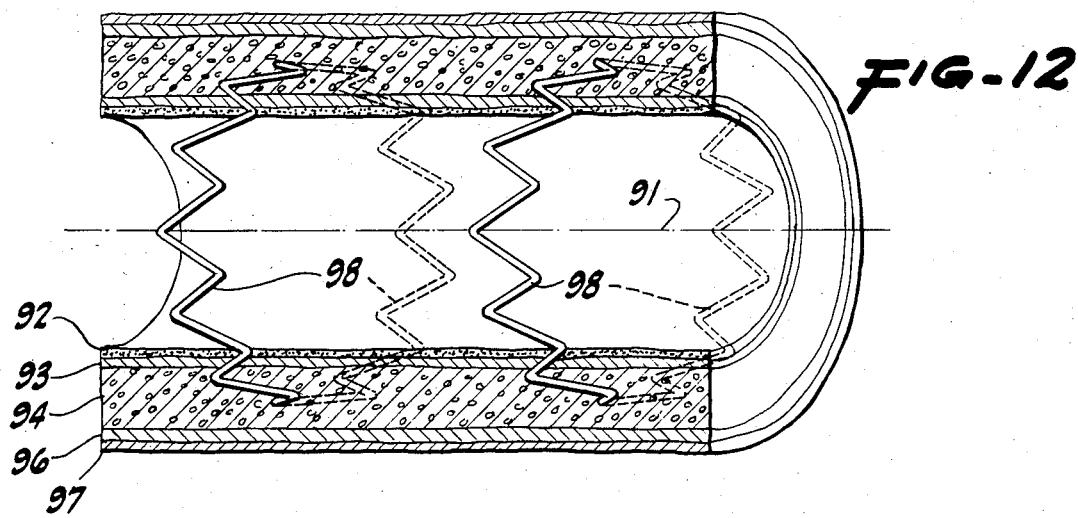
FIG. 12 is an isometric view showing an embodiment with hoop reinforcements.

As shown particularly in FIG. 12, there is arranged around an axis 91, as before, first an inner surface zone 92, followed by an impervious zone 93, a relatively porous, thick zone 94, a relatively solid outer zone 96 and finally an outside, thin, elastomeric zone 97. Particularly, the zone 94 is especially characterized by a number of axially separated, embedded rings 98 to afford hoop strength and to maintain the axial disposition of the materials. The hoops 98 can be of a solid elastomer; of a high density, porous elastomer; or of a rigid plastic such as a polyester. They even can be of metal such as stainless steel wire.

Figure 13:
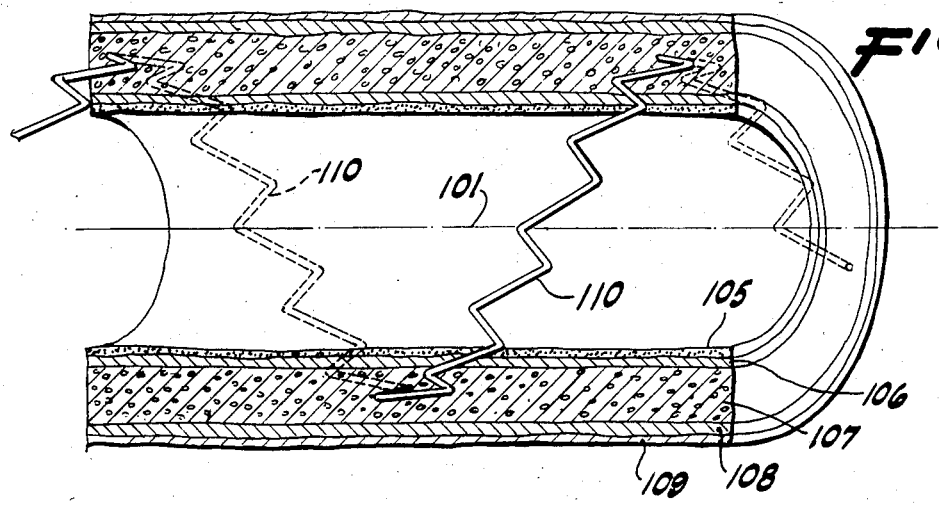
FIG. 13 is a view like FIG. 12 with different-shaped hoops.

A variation on this theme is shown generally in FIG. 13. The central axis 101 is as before and marks the center line of an inner microporous zone 105 within a solid zone 106 in turn within a porous zone 107 surrounded by an outer solid zone 108 and an encompassing tissue interface 109. In this instance, there are inclined hoops 110. Instead of being circular in axial cross-section as the hoops 98 of FIG. 12, the hoops 110 are rather of a radially elongated cross section approximately elliptical in pattern. The artery so furnished is relatively strong in a radial direction or against radial pressure.

Figure 14:
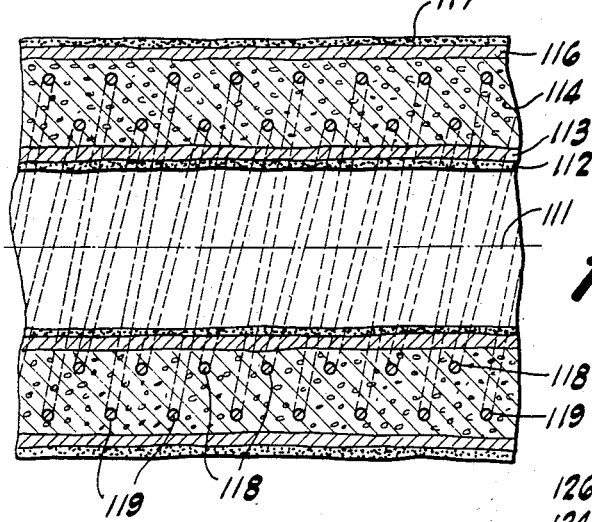
FIG. 14 is a view like FIG. 1 with a plurality of internal concentric helical reinforcements.

In a similar arrangement in FIG. 14, around the central axis 111 is substantially the same arrangement of zones 112, 113, 114, 116 and 117. In addition, there is an inner helical body 118 of wire, plastic or elastomer as well as a surrounding, outer helical body 119. Because of the different diameters of the helical bodies, the pitches of their individual convolutions vary somewhat. The general homogeneity of the blood vessel wall is not adversely affected by the periodical appearance of the reinforcements.

Figure 15:
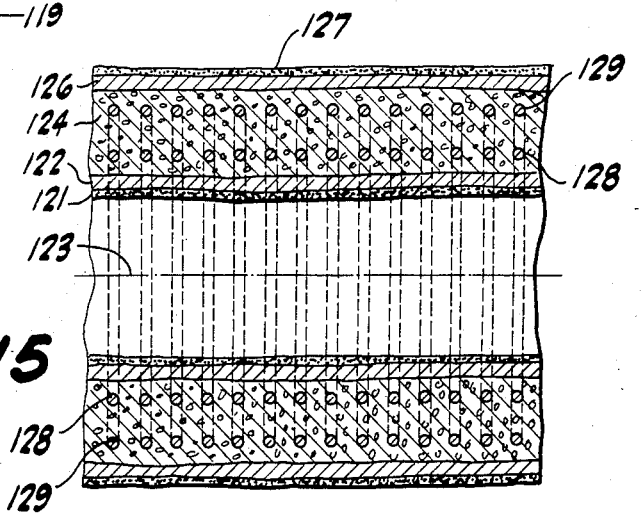
FIG. 15 is a view like FIG. 14 in which the reinforcements are concentric hoops rather than helical.

As a variation on this theme, there is provided, as shown in FIG. 15, a comparable arrangement in which the various zones 121, 122, 124, 126 and 127 are symmetrical about a through axis 123. In this instance, the reinforcements are again in the generally porous central zone 124 and comprise wires 128 and 129, of either metal, elastomer or plastic disposed near the center and outside respectively. These wires form nested, circular rings. There is no axial transmission of forces longitudinally along the length of the FIG. 15 tube by the separate rings 128 and 129, as there may be along the convolutions 118 and 119 in the FIG. 14 version.

Figure 16:
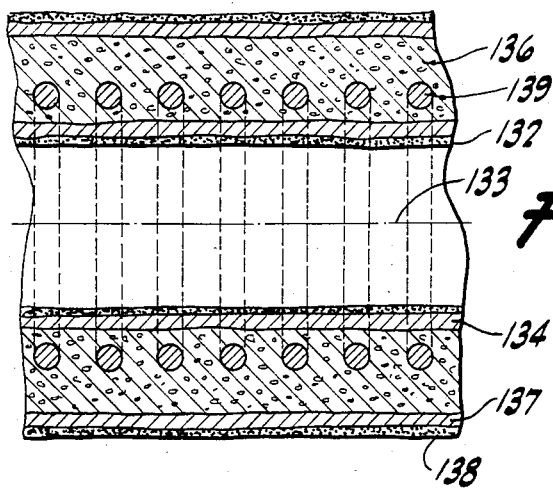
FIG. 16 is like the FIG. 14 version, but the reinforcement is by a single row of rings rather than by a pair of coaxial helices.

In the FIG. 16 version, the zones 132, 134, 136, 137 and 138 are disposed about an axis 133. Symmetrical with the axis 133 are reinforcing rings 139. This arrangement is not especially restricted longitudinally, but is restricted circumferentially.

Figure 17:
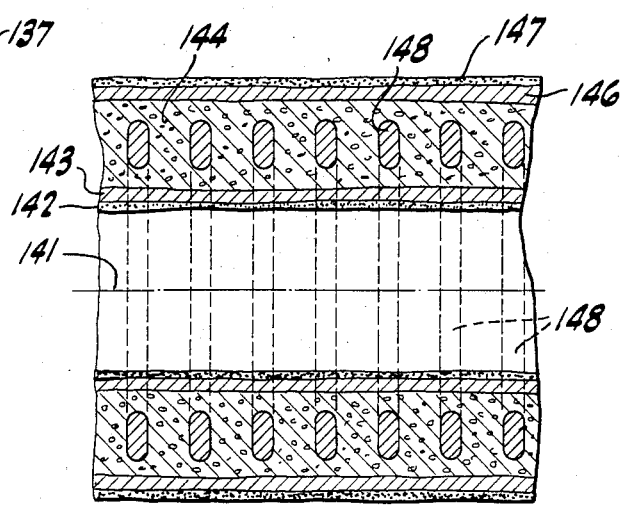
FIG. 17 is like the FIG. 16 arrangement but the reinforcing rings are of a flat stock rather than round stock.

In the arrangement of FIG. 17 the axis 141 is encompassed by the various zones 142, 143, 144, 146 and 147. Within the zone 144 and around the axis 141 are spaced rings 148 of flat wire or plastic stock. Again, these are not constrictive in an axial direction, but, even more than the FIG. 16 version, afford substantial radial restriction.

With all of these arrangements, it is found that the objects of the invention are in general met, and that the natural arterial construction can be replaced by any of the constructions shown herein keeping in mind that the various forms of reinforcement may be utilized not only in the more complex joined zones of material, and any of the reinforcements described could be included in such a simple structure. Due regard may be had to the relative dimensions in diameter and length involved. Taken into appropriate account should be the juxtaposition of the various materials and their own individual and relative dimensions. It has been found that substantially impervious, long-lived blood carrying vessels effective under normal human pressures and conditions are well provided in each instance.

I claim:

1. An arterial graft prosthesis formed of a core zone of porous elastomer disposed about the longitudinal axis of the prosthesis, an inner zone of solid elastomer concentric with and homogeneously joined to the inside of said core zone, an outer zone of porous elastomer, said outer zone of porous elastomer being concentric with and homogeneously joined to the outside of said core zone.

2. An arterial graft prosthesis as defined in claim 1, together with a blood interface zone of microporous elastomer concentric with and homogeneously joined to the inside of said inner zone of solid elastomer.

3. An arterial graft prosthesis as defined in claim 2 wherein said blood interface zone defines pores having a diameter and depth of from 5 to 100 microns.

4. An arterial graft prosthesis as defined in claim 2 wherein the surface of said blood interface zone is hydrophilic.

5. An arterial graft prosthesis as defined in claim 4 wherein the surface of said blood interface zone is coated with an antithrombin.

* * * * *